US006852086B2

United States Patent
Atlas et al.

(10) Patent No.: US 6,852,086 B2
(45) Date of Patent: Feb. 8, 2005

(54) DETECTION OF SIGNS OF ATTEMPTED DECEPTION AND OTHER EMOTIONAL STRESSES BY DETECTING CHANGES IN WEIGHT DISTRIBUTION OF A STANDING OR SITTING PERSON

(76) Inventors: Dan Atlas, Mashabim 20, Hod Hasharon (IL), 45102; Gideon L. Miller, 2 Marcus Street, Jerusalem (IL), 92233

(*) Notice: Subject to any disclaimer, the term of this patent is extended or adjusted under 35 U.S.C. 154(b) by 285 days.

(21) Appl. No.: 10/173,437

(22) Filed: Jun. 18, 2002

(65) Prior Publication Data

US 2002/0193707 A1 Dec. 19, 2002

Related U.S. Application Data

(60) Provisional application No. 60/298,379, filed on Jun. 18, 2001.

(51) Int. Cl.[7] .............................................. A61B 5/103
(52) U.S. Cl. ...................................... 600/595; 600/587
(58) Field of Search ................................. 600/587, 595, 600/300, 301; 128/897, 898; 297/217.1, 217.2, 463.2

(56) References Cited

U.S. PATENT DOCUMENTS

| 5,137,027 A | | 8/1992 | Rosenfeld |
| 5,406,956 A | * | 4/1995 | Farwell ........................ 600/544 |
| 5,507,291 A | | 4/1996 | Stirbl et al. |
| 5,676,138 A | * | 10/1997 | Zawilinski ................... 600/301 |
| 5,771,261 A | | 6/1998 | Anbar |
| 5,774,571 A | | 6/1998 | Marshall |
| 5,853,005 A | * | 12/1998 | Scanlon ....................... 600/459 |
| 5,876,334 A | * | 3/1999 | Levy ........................... 600/300 |
| 5,917,180 A | | 6/1999 | Reimer |
| 6,030,347 A | * | 2/2000 | Nakamura et al. ........... 600/552 |
| 6,388,739 B1 | | 5/2002 | Rice |
| 6,450,957 B1 | * | 9/2002 | Yoshimi et al. .............. 600/309 |
| 6,505,522 B1 | * | 1/2003 | Wilssens ................... 73/862.51 |
| 6,547,743 B2 | * | 4/2003 | Brydon ........................ 600/534 |

* cited by examiner

*Primary Examiner*—Charles Marmor

(57) ABSTRACT

Non-obtrusive monitoring apparatus for detecting the emotional stress of attempted deception by a standing or seated subject. The apparatus has sensors for measuring parameters of posture, sway, weight distribution, cardiac function, and respiratory function, and outputs computer-readable data for processing and reporting. Also disclosed are: systems for synchronizing output data with information about questions asked of the subject as well as other interrogation stimuli administered to the subject; and systems for analyzing the output data and interrogation stimuli to identify patterns indicating heightened anxiety.

12 Claims, 3 Drawing Sheets

DETECTION OF SIGNS OF ATTEMPTED DECEPTION AND OTHER EMOTIONAL STRESSES BY DETECTING CHANGES IN WEIGHT DISTRIBUTION OF A STANDING OR SITTING PERSON

The present application claims benefit of U.S. Provisional Patent Application No. 60/298,379 filed Jun. 18, 2001.

FIELD OF THE INVENTION

The present invention relates to the field of non-obtrusive detection of emotional stress of an individual in general, and signs of emotional stress associated with attempted deception by an individual in particular. The invention includes a monitoring apparatus that is positioned beneath a monitored individual who is standing or seated, the apparatus having attached sensors for sensing parameters reflecting changes in preferably at least one of posture, sway, weight distribution, cardiac function and respiratory function of the monitored individual. The sensors are preferably at least one of strain gauges, piezo electric pressure sensors, optical pressure sensors, and other pressure and weight sensors. The monitoring apparatus also includes a unit for receiving signals from the sensors, and for converting them into data into a computer-readable format, and for storing the data in a computer-readable medium. The monitoring apparatus also includes systems for synchronizing the computer-readable data with information about questions asked of the monitored individual or other interrogation stimuli administered to the monitored individual. The monitoring apparatus can also include systems for analyzing the synchronized computer-readable data and interrogation stimuli to identify patterns likely to indicate heightened anxiety induced by specific questions or interrogation stimuli.

BACKGROUND OF THE INVENTION

The present invention relates to the problem of non-obtrusively and rapidly identifying signs of emotional stress in an individual, and in particular to rapidly and non-obtrusively screening individuals for probability of attempted deception and malevolent intent.

For example, to reduce the risk of terrorism or other malfeasance by providing a tool to help in the security-screening of airline passengers, such tool giving a rapid indication of suspicion that a given passenger may be attempting to deceive a security screening officer. The invention would also be useful at border-crossings and other sensitive, high-traffic locations.

Security screening of airline passengers has become a critical priority since Sep. 11 2001. However, the techniques that are currently available to accomplish this are problematic:

Screening for weapons is insufficiently reliable, as demonstrated by the ease with which the September 11 terrorists and the later "Shoe-Bomber" were able to board aircraft with lethal materials.

Human interpreted questioning of passengers by airline security personnel has low probability of uncovering trained terrorists.

More sophisticated interrogation and "profiling" of passengers is controversial, disruptive to the boarding process, and depends on highly skilled and trained security personnel.

In theory, polygraphic ("liedetection") technologies could be extremely useful for improving airline passenger screening. Polygraphs sense minute changes in physiological signals to indicate a person's level of anxiety as he or she answers questions. A trained polygraphist can use these anxiety measures to identify suspicious answers.

Polygraphic techniques are well known. They are based on detecting and analyzing known physiological correlates of enhanced stress while questioning a subject Common physiological correlates used in conventional polygraphic techniques are changes in respiration, heart-rate, and electrodermal activity (sweat gland activity).

However, conventional polygraphic technologies are not suited to mass-screening applications such as those required for passenger screening at airports. This is because conventional polygraphy techniques are complicated and time-consuming to administer, requiring multiple sensors to be carefully attached to the subject's body. Administering a standard polygraph test to pre-boarding passengers might take several days per airplane.

The following description from the American Polygraph Association, highlights the complex and time consuming nature of standard polygraphy techniques:

It is important to understand what a polygraph examination entails. A polygraph instrument will collect physiological data from at least three systems in the human body. Convoluted rubber tubes that are placed over the examinee's chest and abdominal area will record respiratory activity. Two small metal plates, attached to the fingers, will record sweat gland activity, and a blood pressure cuff, or similar device will record cardiovascular activity.

A typical polygraph examination will include a period referred to as a pre-test, a chart collection phase and a test data analysis phase. In the pre-test, the polygraph examiner will complete required paperwork and talk with the examinee about the test. During this period, the examiner will discuss the questions to be asked and familiarise the examinee with the testing procedure. During the chart collection phase, the examiner will administer and collect a number of polygraph charts. Following this, the examiner will analyze the charts and render an opinion as to the truthfulness of the person taking the test. The examiner, when appropriate, will offer the examinee an opportunity to explain physiological responses in relation to one or more questions asked during the test.—The American Polygraph Association website, Jun. 17, 2002.

In addition to the above procedure, the polygraphic examiner will typically visually observe the subject looking for gross activities (such as fidgeting) that are known to be consistant with stress and therefore elevate suspicion of deception. "Activity sensors" are sometimes used in conjunction with conventional polygraph equipment to assist the examiner in observing such gross activities.

For example the Model 76875AS. Available from Lafayette Instrument Company, 3700 Sagamore Parkway North, Lafayette, Ind. 47903, USA. The following extract from the brochure of the abovementioned activity sensor provides indication of the use of the activity sensor "By providing a graphic record of subject movement, the Activity Sensor allows the polygraph examiner to concentrate on administering the exam instead of trying to observe the subject's movement"—Lafayette Instrument Company New Polygraph Catalog (Downloaded from www.lafayetteinstrument.com/ on Jun. 17, 2002).

In summary therefore, conventional polygraphic technologies are not useful for rapidly and unobtrusively assessing probable deception or emotional arousal in general.

There has been research dedicated towards identifying physiological correlates with stress different from those mentioned above, some of which may require less intrusive wiring of subjects.

U.S. Pat. No. 5,853,005 (Scanlon) teaches building a hydrophone into a seat or chair so as to measure voice stress levels, heart and breath rate, and body temperature for surreptitious interrogation or identification. But these parameters are well studied polygraphic parameters, and are not themselves or in combination known to be sufficient for rapid deception screening.

U.S. Pat. No. 5,137,027 (Rosenfeld.)—Teaches evaluating whether a subject has performed a given act by analyzing P300 brain waves. But this approach requires obtrusive head-mounted sensors.

U.S. Pat. No. 5,507,291 (Stirbl et. al.)—Teaches remotely measuring parameters such as blood pressure, pulse rate, pupil size, respiration rate and perspiration level by transmitting a generated waveform at a remotely located subject and analyzing the result.

U.S. Pat. No. 5,771,261 (Anbar)—Teaches Telethermometric psychological evaluation by monitoring of changes in skin perfusion induced by the autonomic nervous system.

U.S. Pat. No. 5,774,571 (Marshall)—Teaches using a pen incorporating a trembling sensor to ascertain likely signs of stress and therefore deception on the part of the person writing with the pen.

U.S. Pat. No. 5,876,334 (Levi)—Teaches lie detection based on analyzing response time to specific carefully formed questions.

U.S. Pat. No. 6,388,739 (Rice)—teaches of detecting vital-signs of an individual from a distance via a self-referencing microdoppler ladar receiver.

In addition to the above prior-art, reference has been noted in the literature to efforts to assess deception and emotional stress by measuring pupil-dilation, measuring thermal differentials of areas of the face or body, visually analyzing facial expressions, analyzing ocular activities (e.g., eye blinking), and analyzing vocal tremors and other changes in voice characteristics.

However, there are no indications that any of the above less-obtrusive approaches in and of themselves can be sufficiently rapid and reliable to solve the mass screening need described above.

SUMMARY OF THE INVENTION

1—Definitions

For the purposes of this discussion we define the term "footprint" to mean the contact area between the part of the human body (clothed or bare, supported by furniture or unsupported) and a surface upon which it rests. For example, "footprint" may refer to the boundary area between the sole of one foot and the surface upon which the person is standing. As another example, "footprint" may also refer to the boundary area between the soles of both feet and the surface upon which the person is standing. As another example, "footprint" may also refer to the boundary area between the buttocks of a person and the seat upon which the person is sitting. As another example, "footprint" may also refer to the boundary area between the arms of a person and the armrests of the chair seat upon which the person is sitting. As another example, "footprint" may also refer to the boundary area between the legs of a chair upon which a person is sitting, and the surface upon which the chair is positioned.

We define the term "trigger" to mean a cognitive stimulus that causes emotional stress to a given individual 2—Brief Description of the Invention The present invention is generally directed to satisfying the needs set forth above and the problems identified with current intrusive polygraphy systems, especially in environments where a rapid and unobtrusive assessment of likely deception is required.

The problems of having to attach sensors and probes directly to the person being interviewed are resolved by the present invention.

It is an object of the present invention to detect signs of emotional stress by detecting their correlates in subtle shifts in body weight, sway, and posture.

It is a further object of the present invention to detect such signs of emotional distress during an interview or interrogation, so as to indicate probability of attempted deception on the part of the interviewee.

It is well known in the literature that emotional stress leads to a number of physiological responses. This set of physiological responses to emotional stress is often referred to in the literature as the "fight or flight" response, because it has to do with the body automatically preparing itself for physical action. As mentioned above, several of the fight-or-flight responses such as changes in heart rate and respiration have been widely used in conventional polygraphic techniques.

Among the known "fight or flight" responses, are subtle involuntary muscle tensing, body sways, and shifts in weight from foot to foot. For example, emotional stress is known to cause rapid changes in the distribution of weight from the heel towards the toe. This phenomenon is believed by some psychologists to reflect the body's preparation for escape through running. Similarly, abrupt, barely perceptible changes of lean angle are known to occur when a person lies. Such involuntary movements form part of the "body language" of an individual, i.e., the manifestation in movement or posture of emotional states. When such elements of body language betray the spoken word, "leakage" is said to occur.

It is important to note that many such leakages are barely perceptible to the untrained naked eye because the changes in sway and posture that they reflect are very small. Therefore, although they have been studied using video and other recording techniques, and although highly skilled interrogators may consciously look for some of them, until now they have been very difficult to use within practical systems for detecting emotional stress. It is an object of the present invention to enable the detection and usage of such 'leakage' via pressure changes detected at the points where the human body contacts surfaces while standing or sitting.

Because a standing body represents tens of kilograms concentrated on a small "footprint" (the contact boundary between the sole of the foot and the surface that the body is standing on), slight deviations in posture and slight sways of the upper body are reflected in measurable pressure deviations at the contact boundary between the feet and surface they are standing on. Similarly, the contact boundary between buttocks and seat cushion, or between chair leg that someone is sitting on and floor are areas where it is possible to detect very slight variations in posture and sway through their influence on pressure changes.

Modem pressure sensors, such as high-capacitance piezo-electric sensors, or high sensitivity fiber-optics sensors are sensitive enough to resolve weight distribution changes of less than 0.01% of total body weight, and are therefore sensitive enough to detect the above-mentioned deviations in pressure distribution at the footprint. In particular, Kinotex optical sensors, such as those sold by Canpolar East Inc., at 702 Water Street, St Johns NF, Canada, and described in U.S. Pat. No. 5,917,180 are valuable for this purpose. Similarly, high capacitance piezo-electric sensors can be used, as well as strain-gauges.

It should be noted that the fight-or-flight response is not the only source of changes to pressure distribution at the footprint. The standing body continually expresses small background shifts and sways. In addition, head, neck, mouth, and hand movements during speech cause changes in pressure distribution at the footprint In addition, respiration cause slight changes in pressure distribution at the footprint.

Various sources of changes in pressure distribution at the footprint including those mentioned above can be separated by spectral analysis. For example, the pressure changes reflective of the fight-or-flight response tend to be at frequencies reflective of mental processors, and are therefore relatively high frequency. By contrast, the background shifts and sways that the standing body constantly expresses are of typically lower frequency. While higher frequency than background pressure changes, those reflective of the fight-or-flight response tend to be at significantly lower frequencies than those caused by moving the jaw, mouth structures, and head while talking. Therefore, the changes of pressure distribution at the footprint reflective of the fight-or-flight response can be distinguished from other sources of pressure distribution changes by spectral analysis. The pressure change correlates of flight-or-fight responses can also be analyzed by commonly-available expert system software.

The present invention utilizes the abovementioned pressure changes characteristic of "fight-or-flight" response as they coincide with certain "triggers" (phrases, words, questions, or images presented to a subject during a screening interview or other procedure). Such coincidence can be analyzed to indicate an elevated probability that the trigger has particular significance for the subject, and an elevated probability that the subject may be attempting deceit.

In addition, the present invention will preferably detect changes in respiratory patterns of a subject undergoing an interview, such as breath slowing, breath holding, etc. known in conventional polygraphy as being correlated with attempted deception, by identifying their effects on pressure changes at the footprint. The present invention will therefore be able to utilize such known indicators of emotional stress without requiring the obtrusive wiring and tubing of conventional polygraphic techniques.

By amplification and filtering of the abovementioned pressure distribution shift signals a unique parameter is retrieved—namely the body sway vector. The body sway vector is a minute fraction of the weight, ever shifting in amplitude and direction as the person ever-adjusts the posture and breathes, whether standing or seating.

Upon questioning, the verbal response of the interviewed person may be a lie or attempted deception. The body language then betrays the verbal utterance, "leaking" information through changes in the body sway vector. A very small fraction of the person's weight, becomes more pronounced as the person unknowingly shifts the weight distribution between the two feet and between heels and toes. The spectrum-analyzed respiratory patterns show a drop in frequency and amplitude. A correlated change in both channels, subtracted from baselines, indicates possible attempted deception in response to a question.

In addition, the present invention will preferably detect changes in heart rate of a subject undergoing an interview, known in conventional polygraphy as being correlated with attempted deception, by identifying its effects on pressure changes at the footprint. The present invention will therefore be able to utilize such known indicators of emotional stress without requiring the obtrusive cuffs and sensors of conventional polygraphic techniques.

BRIEF DESCRIPTION OF THE FIGURES

The present invention may be understood more fully by reference to the following detailed description of preferred embodiments of the present invention, illustrative examples of specific embodiments of the invention and the appended figures in which.

DESCRIPTION OF PREFERRED EMBODIMENT

Figure 1:
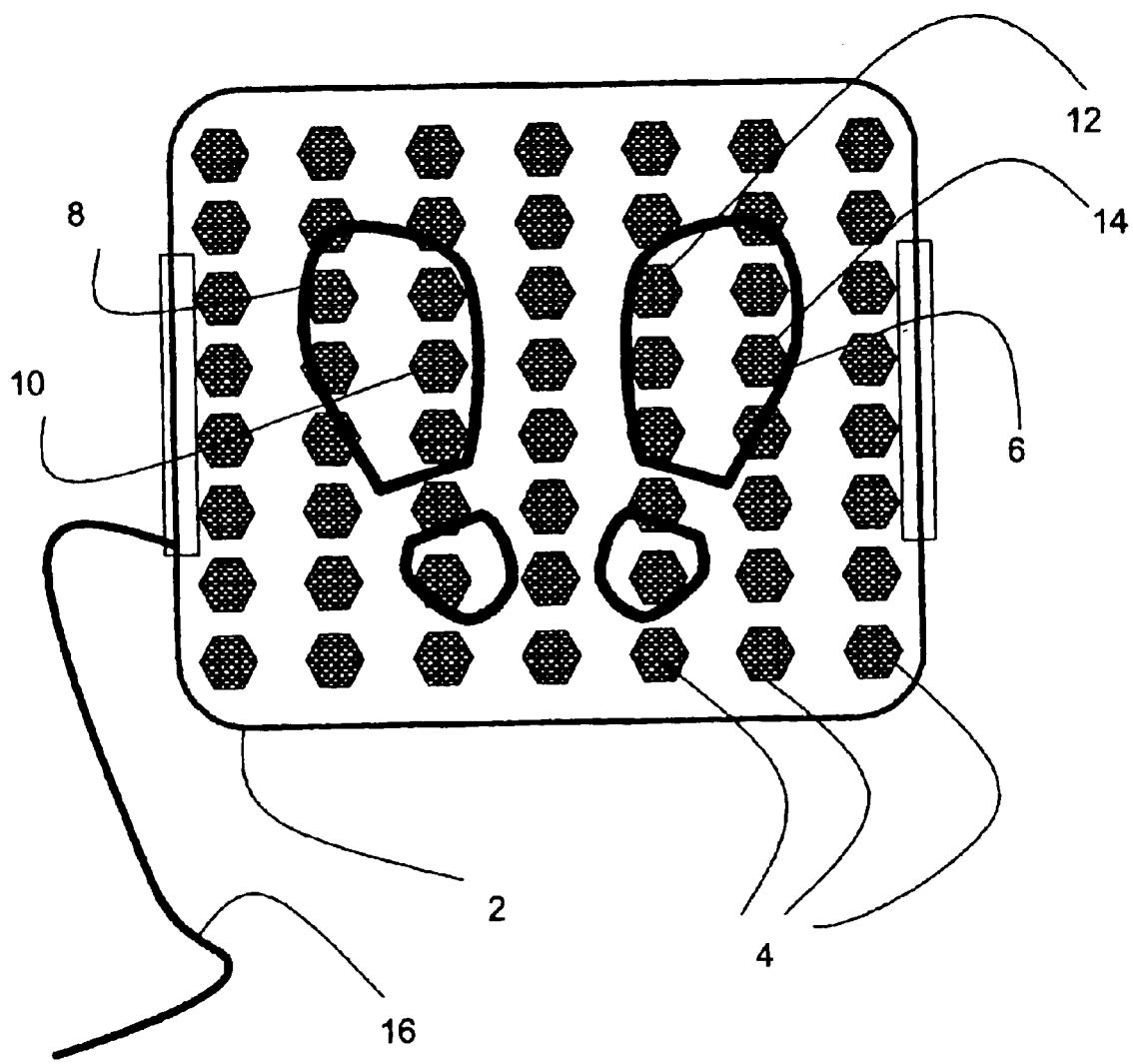
FIG. 1 illustrates a top down view of a preferred monitoring apparatus constructed in accordance with to the present invention.

With reference to FIG. 1, there is illustrated a form of the device constructed in accordance with the invention as one preferred embodiment. The illustrated device contains a flat surface 2, embedded with a plurality of pressure sensors 4, arranged in close proximity to one another for example in the form of a grid of sensing cells, each cell sized 2 square centimeters. An individual stands with his or her feet 6, 8, on said flat surface, or is seated on a chair (not shown) the legs of which are situated on said flat surface during an interview. Body sways and postural changes and respiration are reflected in changes in pressure applied to sensors that lie under said individual's feet 10, 12, 14 and sensors which lie under the legs of said chair (not shown). A cord 16, which may be concealed, connects said sensors and the device with outside power sources and processing and display equipment.

A standing frame (not shown), similar to a door-frame, may optionally be attached to said flat surface, in order to solicit a response known in the art whereby telling a lie commonly causes a person to lean slightly towards a nearby vertical surface.

Figure 2:
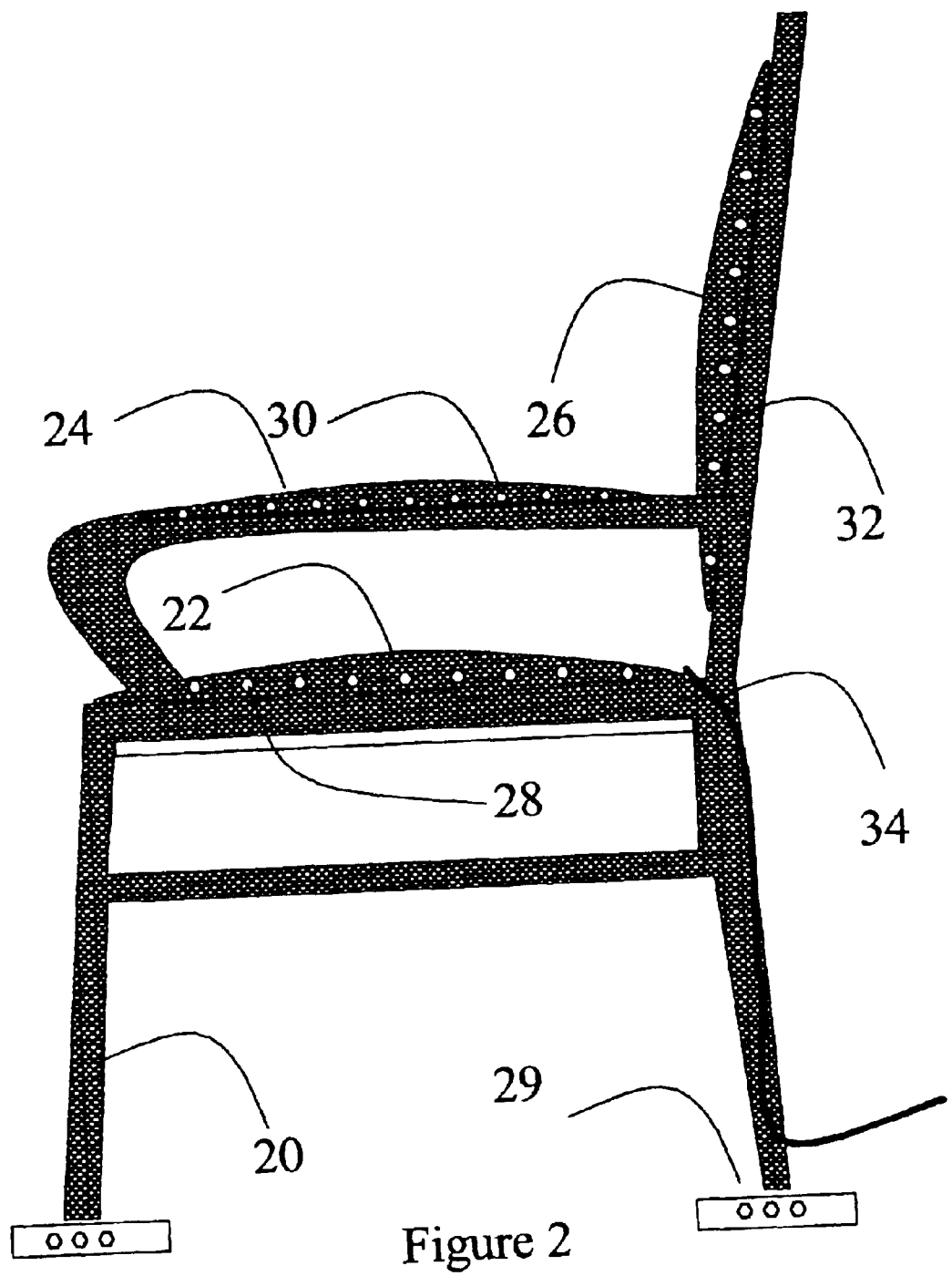
FIG. 2 illustrates a side view of a preferred monitoring apparatus constructed in accordance with to the present invention.

With reference to FIG. 2, there is illustrated a form of the device constructed in accordance with the invention as one preferred embodiment. The illustrated device contains a chair 20, with a seat cushion 22, and optionally arm and back cushions, 24 and 26, within which are embedded a plurality of pressure sensors, 28, 30, 32, arranged in close proximity to each other, for example in the form of a grid of sensing cells, each cell sized 2 square centimeters. Optionally, a sensor array 29, is placed underneath each leg of the chair. A cord, 34, which may be concealed, connects said sensors and the device with outside power sources and processing and display equipment.

Figure 3:
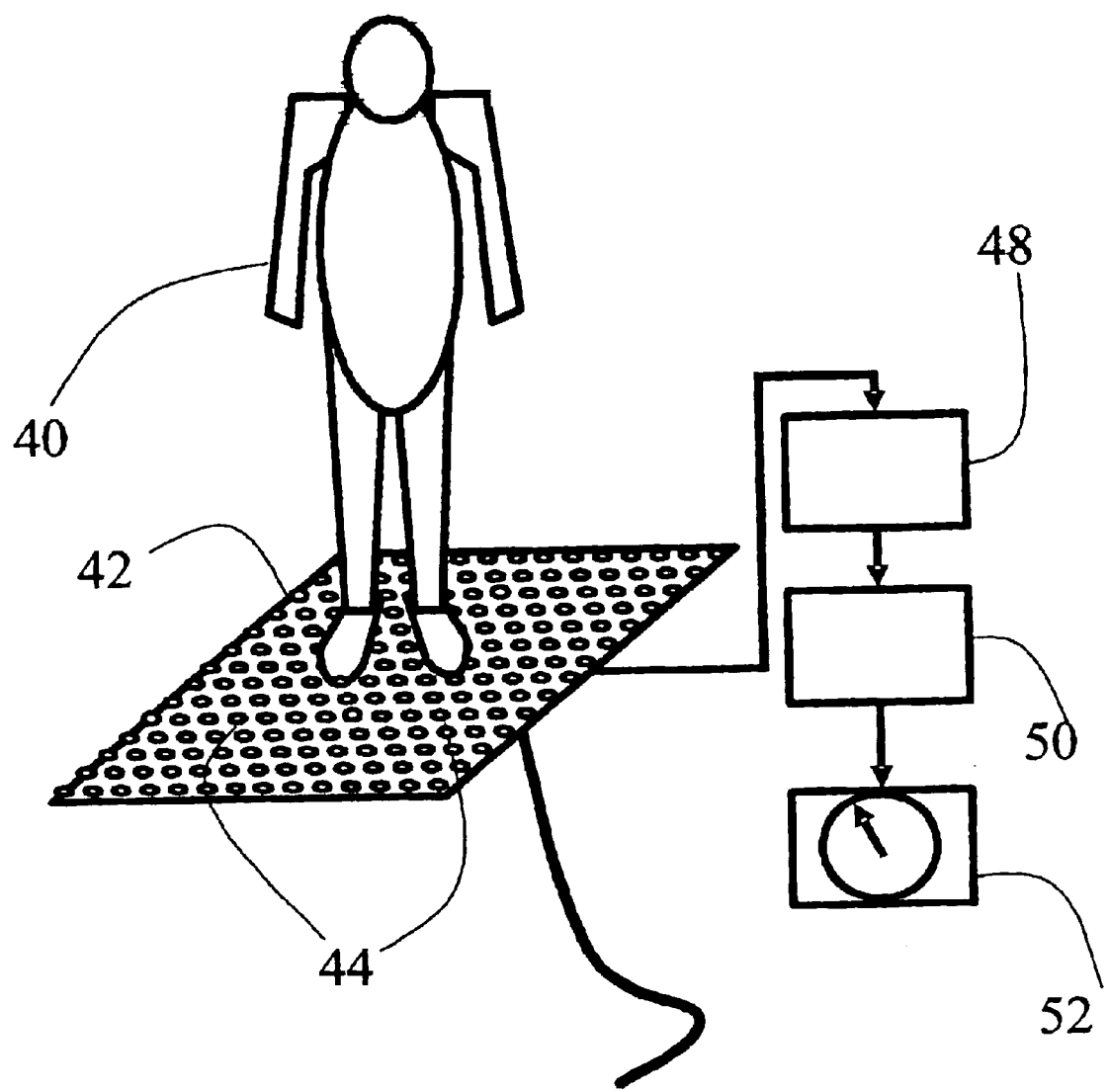
FIG. 3 illustrates a system according to the present invention.

FIG. 3 is a simplified block diagram illustrating the operation of the device shown in FIG. 1. An individual, 40, is caused to stand upon the flat surface, 42, said surface being embedded with a plurality of connected pressure sensors, 44. The individual may be instructed to stand still during the interview process. The interview process may have several stages including a system test stage and a baseline stage during which neutral stimuli are presented, and an interrogation stage during which both neutral and trigger stimuli are presented. The sensors, 44, sense signals reflecting changes in pressure during the interview process. The signals are filtered and amplified via a preamplifier 48 to a signal conditioning processor, 48 which includes amplifiers and filters bank which extracts the attributes of the body sway vector as well as respiration signals, and the processed signals are then digitized and then serially transmitted to a computer 50, where patterns of pressure changes are analyzed together with information about the timing of neutral and trigger stimuli to determine likely emotional stress. Such analysis may include identifying pressure changes reflective of abrupt changes in lean-angle, and pressure changes reflective of abrupt changes in respiration patterns, and pressure changes reflective of abrupt changes in weight distribution between heel and toe and between feet or amongst legs of a chair and feet, and other pressure changes that are reflective of "flight-or-fight" responses. Measures of emotional stress are displayed on a display, 52, for example to a security screening officer located in the proximity of said display. A flag may be displayed on the display indicating that said measures of emotional stress in response to trigger stimuli indicate an elevated probability that said subject attempted to deceive the interviewer during the interview process. A flag may further suggest that said subject be directed to more extensive review and inspection.

Although the invention has been described in detail for the purpose of illustration, it is to be understood and appreciated that such detail is solely and purely for the purpose of example, and that many other variations, modifications and applications of the invention can be made by those skilled in the art without departing from the spirit and scope of the invention.

What is claimed is:

1. A method for detecting emotional stress of a human subject in response to cognitive stimuli by measuring variations in the pressure distribution across the subject's footprint, the method comprising:
   (a) causing the subject to apply force on a flat surface, said flat surface having embedded therein a plurality of pressure sensitive sensors;
   (b) connecting said pressure sensitive sensors to a signal analysis processor;
   (c) presenting the subject with cognitive stimuli, the subject's disposition to which is of interest in the context of a given interview;
   (d) monitoring variations in pressure distribution between said sensors, and deriving variation signals therefrom;
   (e) filtering said variation signals to derive filtered variation signals; and
   (d) matching said filtered variation signals to a pattern that represents emotional stress.

2. The method of claim 1, wherein said subject sits in a chair, and at least one leg of said chair is positioned on said flat surface.

3. The method of claim 1, wherein said flat surface is a mat.

4. The method of claim 3, wherein said mat is embedded in a chair and said subject sits in said chair.

5. The method of claim 4, wherein a plurality of said mats is used and the subject touches different mats of said plurality of mats with different parts of his or her body.

6. The method of claim 5, wherein at least one leg of said chair is positioned upon at least one mat of said plurality of mats.

7. A system for detecting emotional stress of a human subject, in response to cognitive stimuli by measuring variations in pressure distribution across the subject's footprint, the system comprising:
   (a) a flat surface having embedded therein a plurality of pressure sensitive sensors;
   (b) a signal conditioning processing means coupled to said pressure sensitive sensors for detecting shifts in the subject's weight distribution according to signals from said pressure sensitive sensors;
   (c) a signal analysis processing means coupled to said signal conditioning processing means, said signal analysis processing means for analyzing said shifts in weight distribution to detect patterns indicative of emotional stress; and
   (d) a display coupled to said signal analysis processing means.

8. The system of claim 7, wherein at least one of said sensors is a high-capacitance piezo electric pressure sensor.

9. The system of claim 7, wherein at least one of said sensors is a fiber-optic pressure sensor.

10. The system of claim 7, wherein at least one of said sensors is a strain gauge.

11. The system of claim 7, wherein said signal analysis processing means includes software operative to identify pressure change correlates of flight-or-fight responses.

12. The system of claim 11, wherein said software is expert system software.

* * * * *